(12) United States Patent
Sweitzer

(10) Patent No.: US 12,035,923 B2
(45) Date of Patent: Jul. 16, 2024

(54) SURGICAL TOOL HANDLE ASSEMBLY

(71) Applicant: Shukla Medical, St. Petersburg, FL (US)

(72) Inventor: Zachary Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 399 days.

(21) Appl. No.: 17/451,665

(22) Filed: Oct. 21, 2021

(65) Prior Publication Data

US 2022/0039807 A1 Feb. 10, 2022

Related U.S. Application Data

(63) Continuation of application No. 16/549,896, filed on Aug. 23, 2019, now Pat. No. 11,154,306.

(60) Provisional application No. 62/722,458, filed on Aug. 24, 2018.

(51) Int. Cl.
*A61B 17/16* (2006.01)
*A61B 17/00* (2006.01)
*B23B 31/20* (2006.01)

(52) U.S. Cl.
CPC ............ *A61B 17/162* (2013.01); *A61B 17/00* (2013.01); *A61B 17/1604* (2013.01); *A61B 17/1613* (2013.01); *A61B 17/1675* (2013.01); *B23B 31/20* (2013.01); *A61B 2017/00367* (2013.01); *A61B 2017/00469* (2013.01); *A61B 2017/00473* (2013.01); *A61B 2017/00477* (2013.01); *A61B 2560/0431* (2013.01); *B23B 2231/2005* (2013.01)

(58) Field of Classification Search
CPC ......................... A61B 17/1604; A61B 17/162
See application file for complete search history.

(56) References Cited

U.S. PATENT DOCUMENTS

| | | | | |
|---|---|---|---|---|
| 3,618,962 A | * | 11/1971 | Cox | B23B 31/202 |
| | | | | 279/97 |
| 8,286,970 B2 | * | 10/2012 | Frey | A61B 1/00135 |
| | | | | 279/43.4 |
| 9,414,848 B2 | * | 8/2016 | Edwards | A61B 17/162 |
| 2004/0106845 A1 | * | 6/2004 | Anderson | A61F 2/0045 |
| | | | | 600/30 |
| 2014/0336717 A1 | * | 11/2014 | Predick | A61B 17/56 |
| | | | | 606/86 R |
| 2021/0106423 A1 | * | 4/2021 | Whitman | A61B 17/0487 |

* cited by examiner

*Primary Examiner* — Christian A Sevilla
(74) *Attorney, Agent, or Firm* — Kim IP Law Group LLC

(57) ABSTRACT

A handle assembly is disclosed for firmly holding a surgical tool. The handle assembly comprises a handle and a locking mechanism attached to the handle. The locking mechanism includes a locking ring, a collet, and a compressible locking pin engageable with the locking ring and collet. The locking ring is moveable between first and second positions relative to the handle. The first position is an unlocked position whereby the locking pin is in a decompressed state relative to the locking ring and the collet. In the first position, a surgical tool may be inserted and withdrawn from the collet of the locking mechanism. The second position is a locked position whereby the locking pin is in a compressed state relative to the locking ring and the collet. In the second position, a surgical tool is anchored in the collet of the locking mechanism.

10 Claims, 13 Drawing Sheets

SURGICAL TOOL HANDLE ASSEMBLY

CROSS-REFERENCE TO RELATED APPLICATIONS

This application is a continuation of U.S. patent application Ser. No. 16/549,896, filed Aug. 23, 2019, entitled "Surgical Tool Handle Assembly," which claims the benefit under 35 U.S.C. § 119(e) of U.S. Provisional Application Ser. No. 62/722,458, filed Aug. 24, 2018, entitled "Knee Osteotome Handle," the disclosures of which are hereby incorporated by reference in their entirety for all purposes.

BACKGROUND OF THE DISCLOSURE

The present disclosure relates generally to a handle for a surgical tool. Specifically, the present disclosure relates to a handle for releasably receiving a surgical tool such as an osteotome and the like.

An osteotome or similar surgical tool is a chisel-like instrument used to cut or divide bone. Conventional handles for holding and manipulating surgical tools, such as osteotomes for the knee and other body parts, do not always provide secure gripping or firm grasping of the surgical tool. That is, the surgical tool is not rigidly connected to the handle or has too much play relative to the handle, thereby resulting in wobbling or other movement of the tool. Consequently, such play can adversely affect control or effectiveness of the tool and ultimately the precision of the surgical procedure being performed.

BRIEF SUMMARY OF THE DISCLOSURE

In accordance with an exemplary embodiment, there is provided a handle assembly for receiving a surgical tool. The handle assembly comprises a handle and a locking mechanism attached to the handle. The locking mechanism includes a locking ring, a collet, and a compressible locking pin engageable with the locking ring and collet. The locking ring is moveable between first and second positions relative to the handle.

An aspect of the exemplary embodiment is that the collet is mounted within the handle and includes a flexible portion moveable between a first position and a second position. When the locking ring moves from the first position to the second position, the flexible portion of the collet moves from the first position to the second position. Further, the compressible locking pin is between the locking ring and the collet. The compressible locking pin includes at least one of nylon, polytetrafluoroethylene, ultra-high molecular weight polyethylene, polyetherimide, or glass.

Another aspect of the exemplary embodiment is that the locking mechanism further includes a retaining ring having a through hole for receiving the locking pin. The locking pin is mounted in the through hole and oversized relative to a size of the through hole. Additionally, the locking pin is mounted in the through hole and has an overall height greater than an overall height of the retaining ring, and the locking mechanism includes a cam for camming against the locking pin.

In accordance with an exemplary embodiment, there is provided a handle assembly for receiving a surgical tool. The handle assembly comprises a handle having a tapered receiving cavity, and a locking mechanism attached to the handle and received within the tapered receiving cavity. The locking mechanism includes a locking ring moveable between first and second positions relative to the handle, a retaining ring, a collet, and a locking pin mounted to the retaining ring and positioned between the locking ring and collet.

An aspect of the exemplary embodiment is that the retaining ring, collet and locking pin are within the tapered receiving cavity. The locking ring includes a cam for camming against the locking pin. Each of the locking ring, retaining ring and collet includes a central through hole for receiving a surgical tool.

Another aspect of the exemplary embodiment is that the locking mechanism further includes a plate between the locking ring and collet, and the locking pin directly engages the locking ring and plate. The locking mechanism further includes a biasing member biasing the collet, and the collet directly engages a tapered wall of the tapered receiving cavity. The locking pin is a deformable locking pin and the collet is a flexible collet.

Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

DESCRIPTION OF THE INVENTION

Figure 1A:
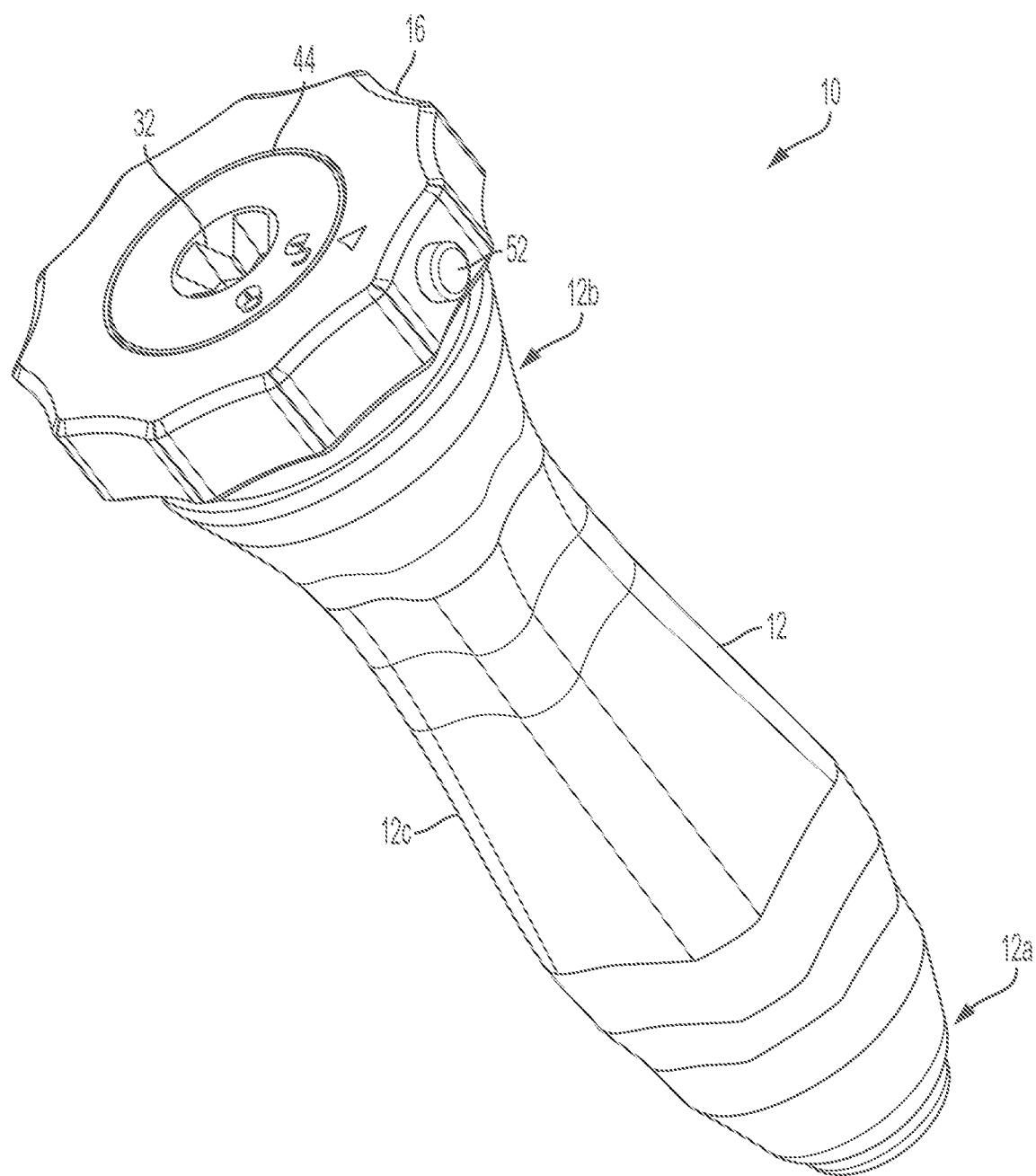
FIG. 1A is a perspective view of a handle assembly for receiving a surgical tool in accordance with an exemplary embodiment of the subject disclosure.

Reference will now be made in detail to the exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. The term "distal" shall mean away from the center of a body. The term "proximal" shall mean closer towards the center of a body and/or away from the "distal" end. With reference to a handle assembly, the "distal end" of the present handle assembly refers to the end of the assembly towards the locking mechanism and the "proximal end" of the present handle assembly refers to the end of the assembly away from the locking mechanism. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 1B:
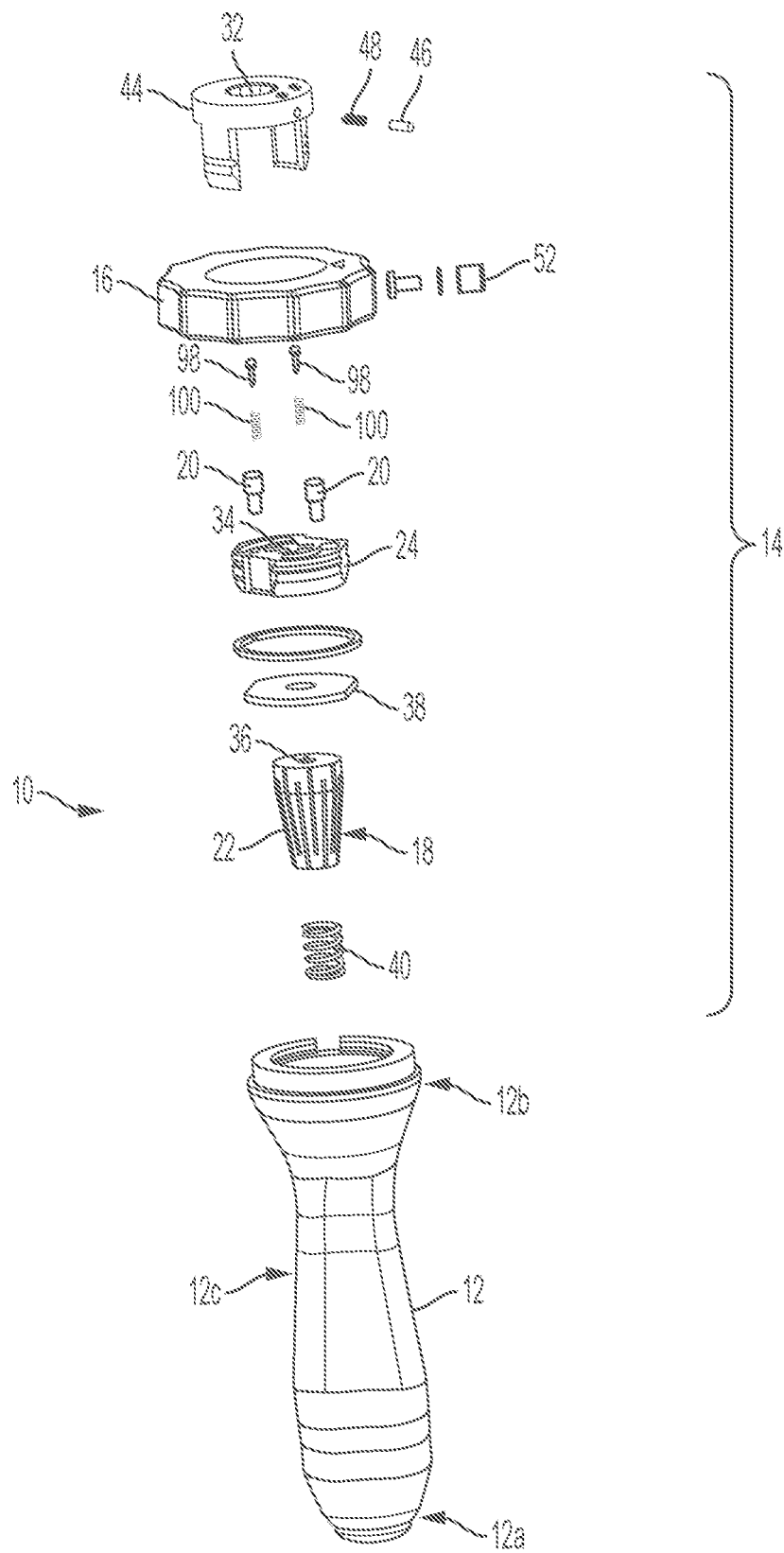
FIG. 1B is an exploded view of the handle assembly of FIG. 1A.

Referring now to the drawings, FIGS. 1A and 1B illustrate a handle assembly 10 for receiving an unillustrated surgical tool such as a knee osteotome or any other surgical tool requiring a stable connection with a handle to facilitate tool manipulation. The handle assembly comprises a handle 12 and a locking mechanism 14 attached to the handle.

Figure 6:
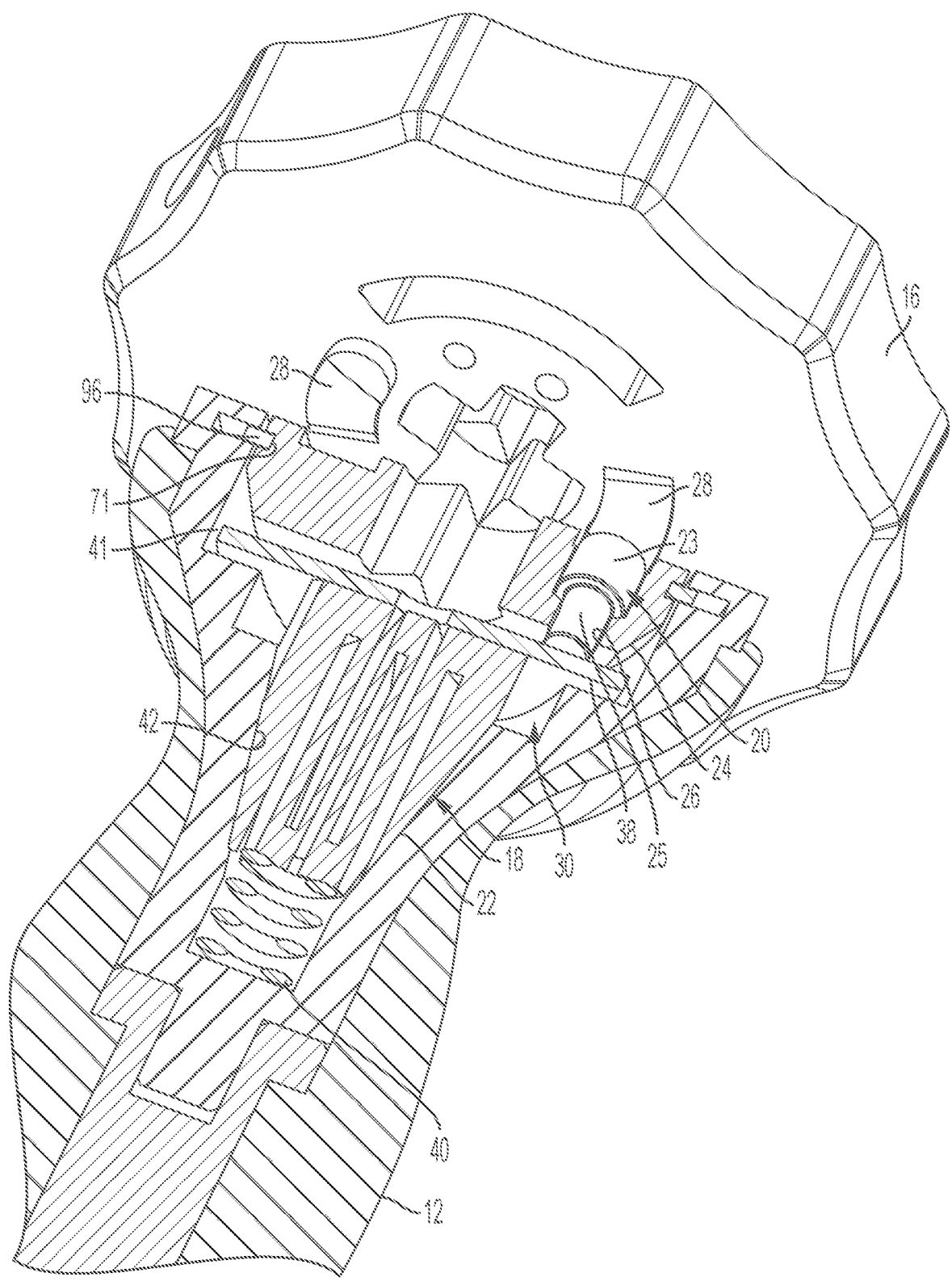
FIG. 6 is a partial longitudinal cross-sectional view of the handle assembly of FIG. 1A.

The handle 12 is an ergonomically shaped handle adapted to be comfortably grasped by a hand of a user. The handle 12 has a proximal end 12a, a distal end 12b adjacent the locking mechanism 14, and a contoured intermediate portion 12c between the proximal and distal ends 12a, 12b. As best seen in FIG. 6, the handle 12 has a tapered receiving cavity 30 extending from its distal end. The tapered receiving cavity includes a counterbore section 41 and a tapered wall 42.

Referring back to FIG. 1B, the locking mechanism 14 includes a locking ring 16, a collet 18, and a deformable or compressible locking pin 20 engageable with the locking ring and collet, as further discussed below. The locking mechanism is attached to the handle 12 and received within the tapered receiving cavity 30 of the handle. Referring to FIGS. 1B and 6, the locking mechanism further includes a retaining ring 24, a central ring 44, a plate 38 between the locking ring and the collet, and a biasing member 40 biasing the collet. Specifically, the locking mechanism is secured to the handle by connection of the central ring's legs 84 lockingly engaging the retaining band 96, as further discussed below.

Figure 2A:
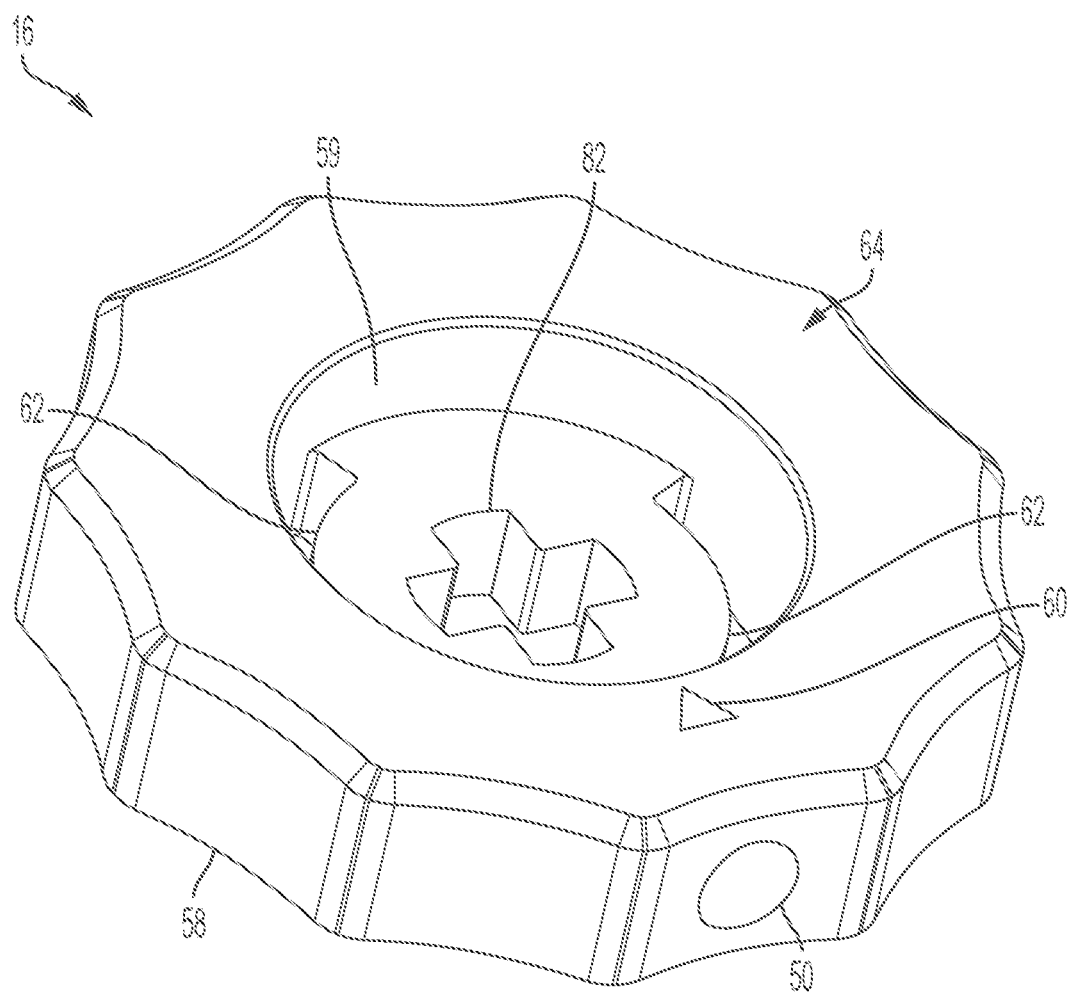
FIGS. 2A-B are perspective views of a locking ring of the handle assembly of FIG. 1A.
Figure 2B:
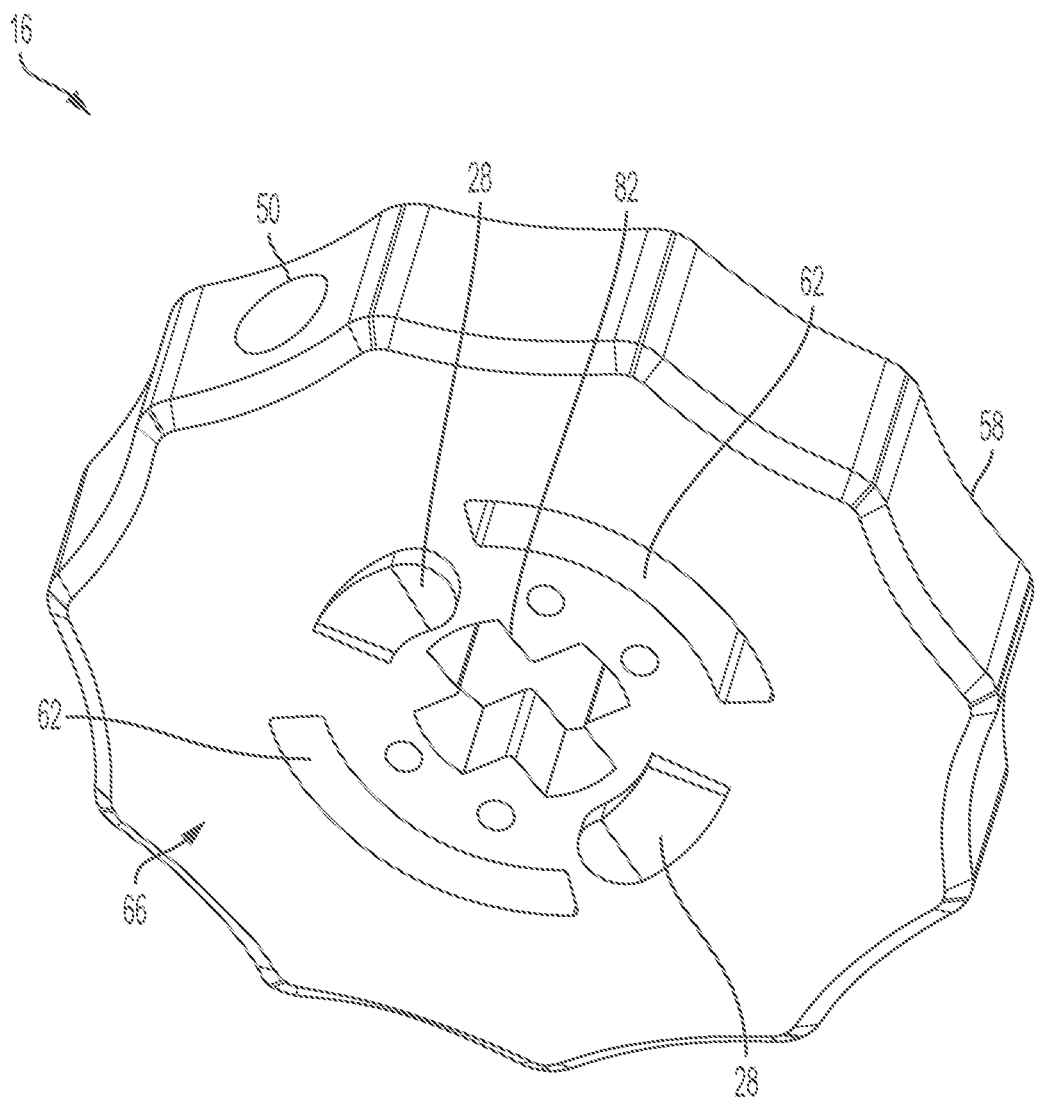

The locking ring 16 is configured as shown, e.g., in FIGS. 1A, 1B, 2A, 2B, and 6. The locking ring includes a distal end 64 and a proximal end 66. In accordance with the exemplary embodiment, the locking ring includes a central counterbore or cylindrical indentation 59 adapted to receive the central ring 44. The locking ring includes a central through hole 82 in the cylindrical indentation for receiving a surgical tool. As shown in FIGS. 2A and 2B, the central through hole 82 is illustrated as substantially cross-shaped, although the central through hole may be shaped in any other shape suitable for receiving a surgical tool, such as a triangular, square, pentagonal, hexagonal, heptagonal, or octagonal through hole.

The locking ring also includes one or more guide through holes 62. The guide through holes 62 are adapted to receive one or more guide legs 84 of the central ring 44 through the locking ring, as further discussed below. In some aspects, the guide through holes 62 are curved along a circumference of the central indentation 59 and disposed opposite each other on either side of the central indentation.

Referring to FIG. 2B, the locking ring 16 also includes a cam 28. The cam is disposed about the undersurface of the locking ring for camming against the locking pin 20. The cam is configured, e.g., as a curved ramp that extends distally from the proximal end surface. That is, the cam extends further than the main undersurface of the locking ring.

The locking ring also includes a bore or opening 50 for receiving a button lock 52 and a position indicator 60 to indicate whether the locking ring is in a first or second position relative to the handle 12. The locking ring further includes scalloped edges 58. The scalloped edges are concave edges and adapted to facilitate rotating or twisting the locking ring from the first to the second position and back again.

Figure 7A:
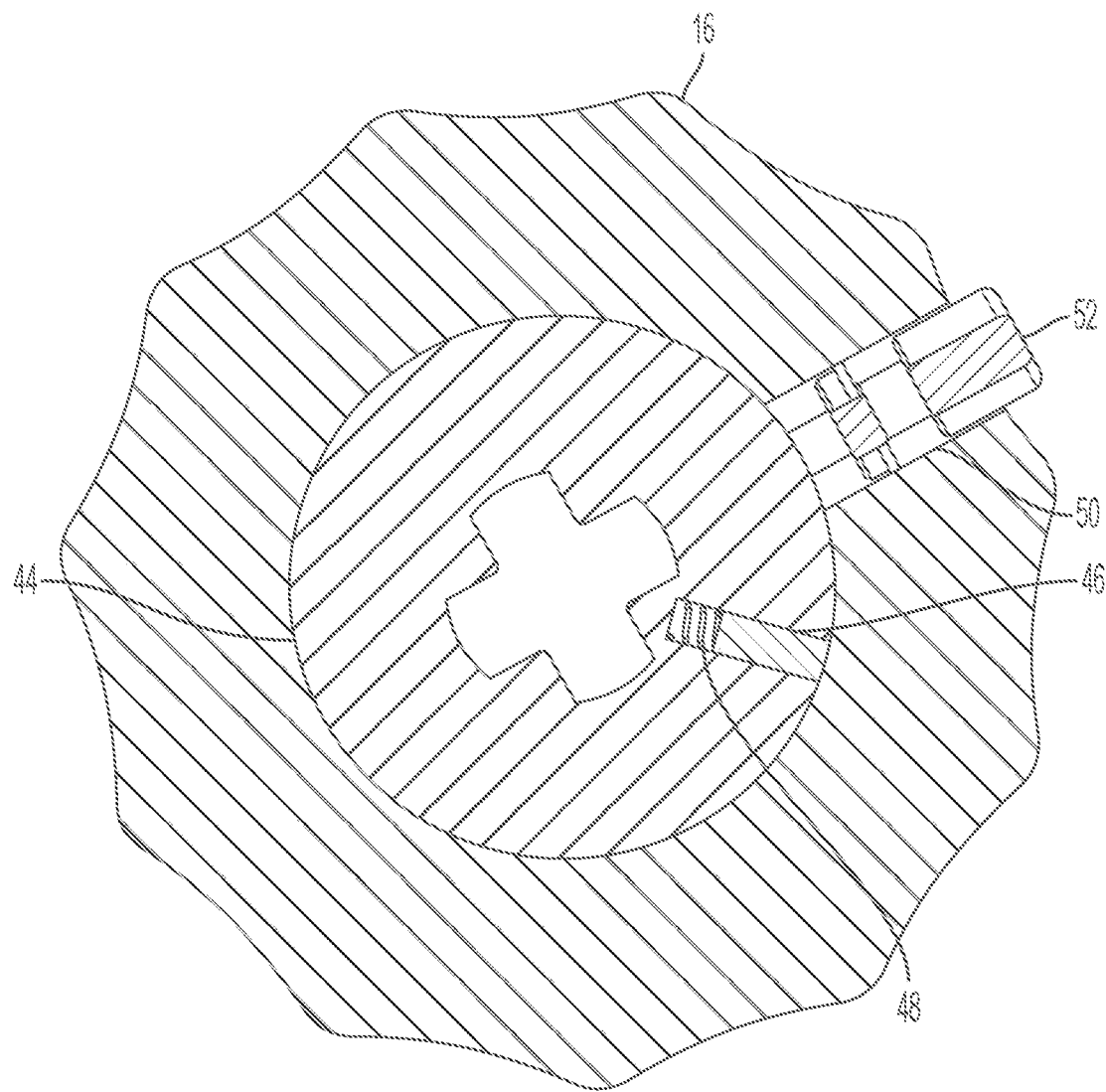
FIGS. 7A-B are various views of a locking ring and central ring of the handle assembly of FIG. 1A in an unlocked position with certain components omitted and in phantom for purposes of illustration.
Figure 7B:
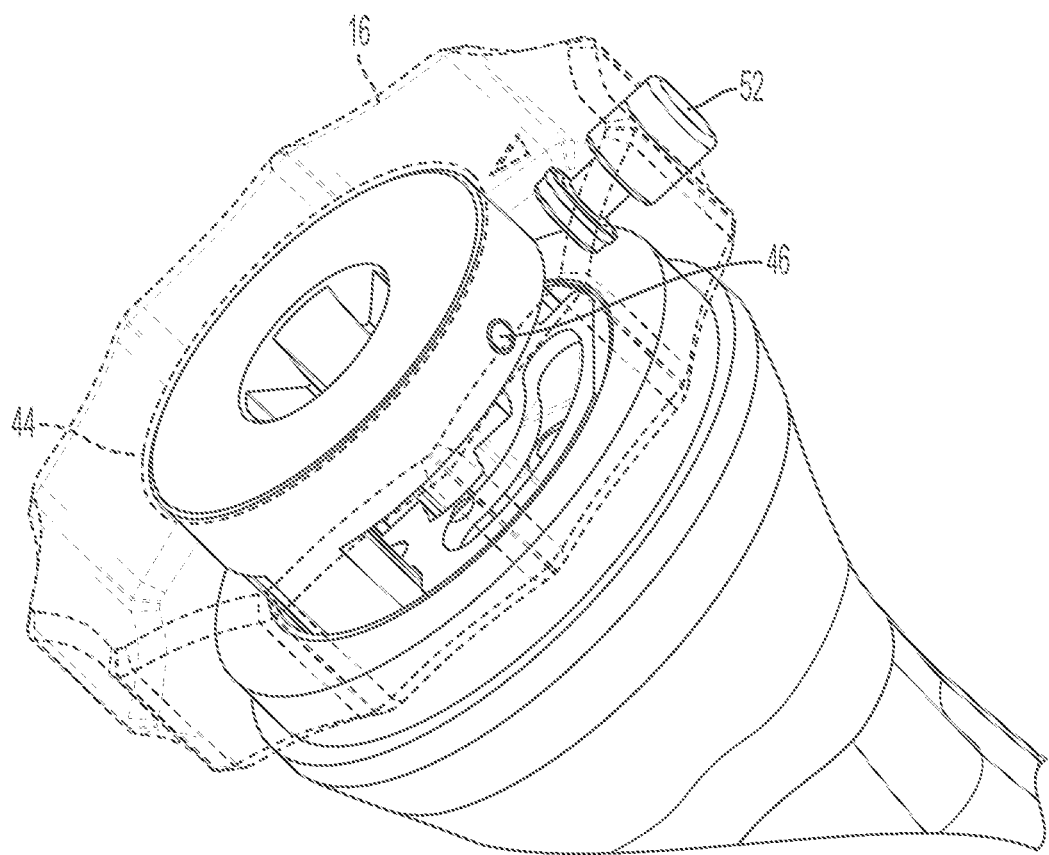
Figure 8:
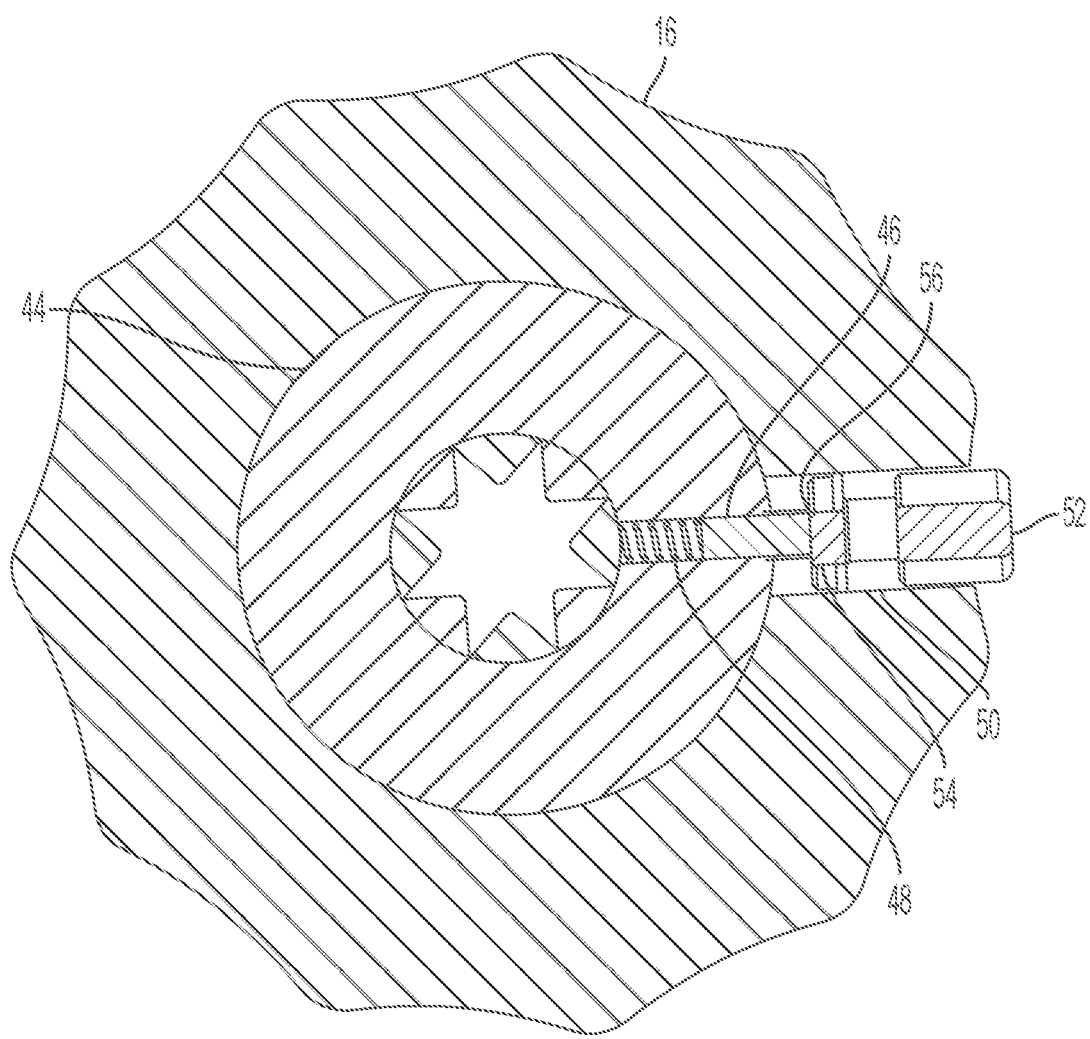
FIG. 8 is a top cross-sectional view of a locking ring and central ring of the handle assembly of FIG. 1A in a locked position with certain components omitted for purposes of illustration.

The locking ring is moveable between first and second positions relative to the handle 12. Specifically, the locking ring is operable to lock and unlock the surgical tool to the handle. FIGS. 7A and 7B illustrate the first position and FIG. 8 illustrates the second position of the locking ring. The first position is an unlocked position and the second position is a locked position, respectively.

Figure 5:
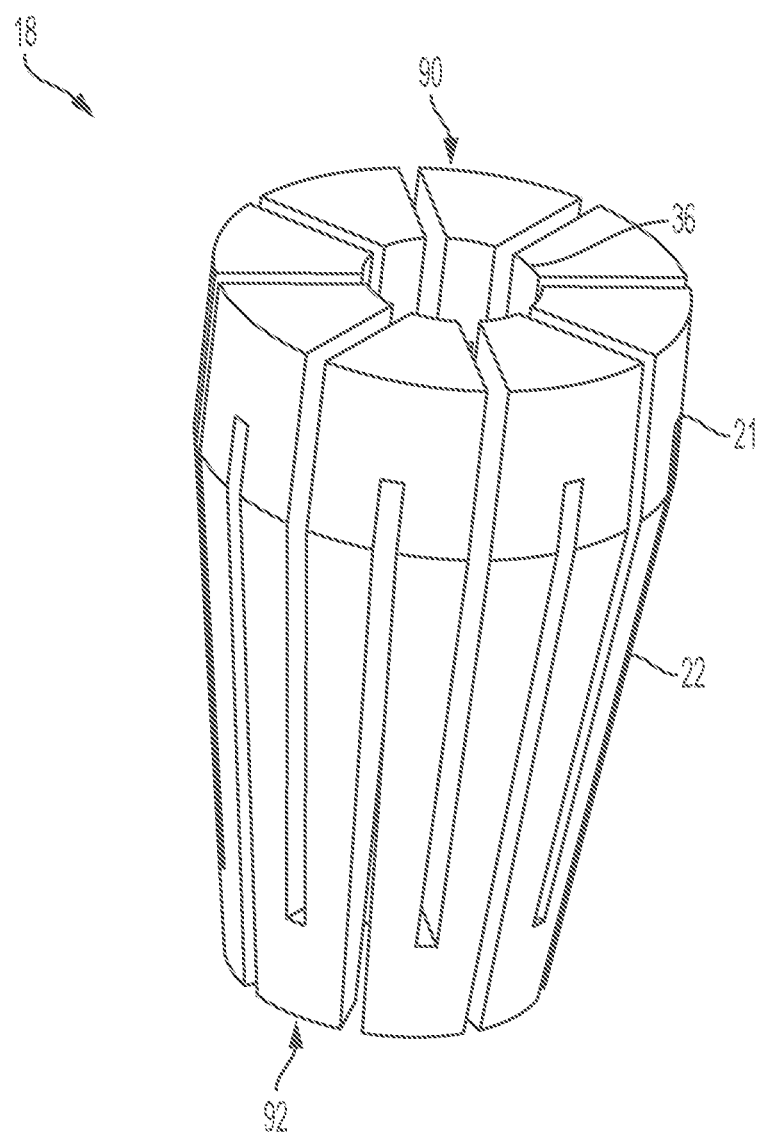
FIG. 5 is a perspective view of a collet of the handle assembly of FIG. 1A.

The collet 18 is configured as shown, e.g., in FIGS. 1B and 5. The collet includes a distal end 90 and a proximal end 92. The distal end includes a main body portion 21 and the proximal end includes a tapered flexible portion 22. In accordance with the exemplary embodiment, the collet is formed from a single piece of material. The collet is formed in an accordion-like fashion along a length of the collet so as to form a plurality of slits extending along the length of the collet along with a central through hole 36. The plurality of slits provide a cage-like structure to the collet. Due to the plurality of slits, the tapered flexible portion is deformable and flexible, e.g., moveable between a first position (e.g., an uncompressed position) and a second position (e.g., a compressed position). The first position of the collet is also a surgical tool receiving position and the second position of the collet is also a surgical tool locking position. The central through hole 36 is configured to receive the surgical tool. When mounted to the handle 12, the collet directly engages the tapered wall 42 of the tapered receiving cavity 30. The collet may be formed from a hard metal such as steel or any other hard metal suitable to be machined so as to be deformable and flexible. Due to the overall configuration and flexibility of the collet, the central through hole diameter can be changed between a first diameter and a second diameter smaller than the first diameter so as to securely engage a tool therein. In other words, the overall diameter of the collet changes between a first diameter and a second diameter when the collet moves between the first and second positions respectively.

The locking pin 20 is a deformable or compressible locking pin. That is, the locking pin while rigid can have its overall dimension changed upon application of forces applied to it by the locking ring 16 as further discussed below, and which is resilient enough to return to substantially its original shape and dimensions upon removal of the application of forces. The locking pin can be configured as best shown in FIGS. 1B and 6. In the present exemplary embodiment the locking pin includes a main body 23 and an anchor portion 25, as shown in FIG. 6. The anchor portion 25 has a smaller diameter than that of the main body 23. According to an aspect, there is at least one compressible locking pin 20. In further aspects, there may be two or more locking pins as shown in FIG. 1B. The locking pin is oversized relative to the size of a through hole 26 in the retaining ring 24. For example, the locking pin is oversized with an overall height greater than an overall height of the through hole 26 and greater than an overall height of the retaining ring 24. The number of locking pins may correspond to the number of through holes 26 of the retaining ring 24 and the number of cams 28 of the locking ring 16. The locking pin directly engages the locking ring 16 and the plate 38 of the locking mechanism 14.

The compressible locking pin 20 may be formed from generally compressible polymers or elastomers. Examples of generally compressible polymers or elastomers can include, but are not limited to, a suitably hard polymer such as nylon, polytetrafluoroethylene (PTFE), glass-filled PTFE, ultra-high molecular weight polyethylene such as Tivar®, polyetherimide such as Ultem®, a glass, or any combination of the foregoing. In accordance with the exemplary embodiment, the locking pin is formed from 25% glass-filled PTFE. For example, the locking pin may have a modulus of elasticity of about 1700 N/mm$^2$ or a Shore hardness of about 65 Shore D. Advantageously, such material exhibits a low coefficient of friction that facilitates the sliding interaction of the locking pin with the cam 28 of the locking ring 16, as further discussed below.

Figure 3A:
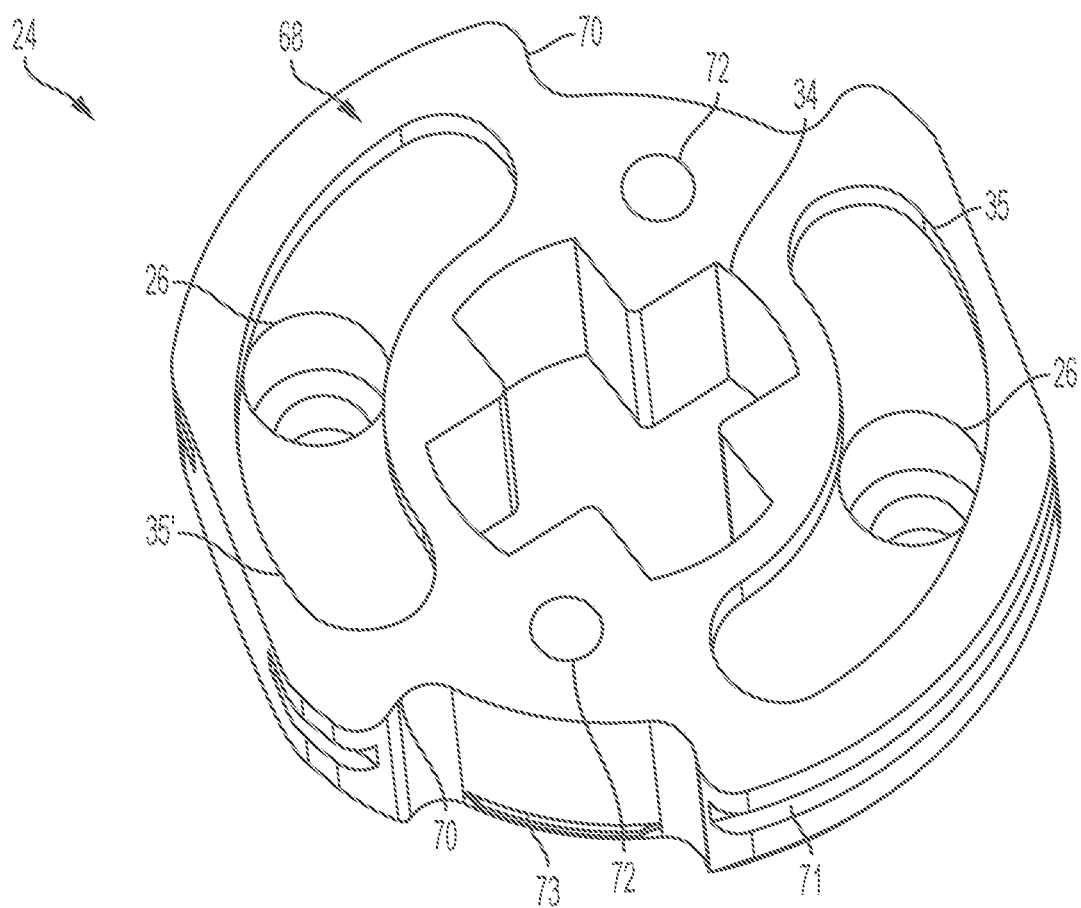
FIGS. 3A-B are perspective views of a retaining ring of the handle assembly of FIG. 1A.
Figure 3B:
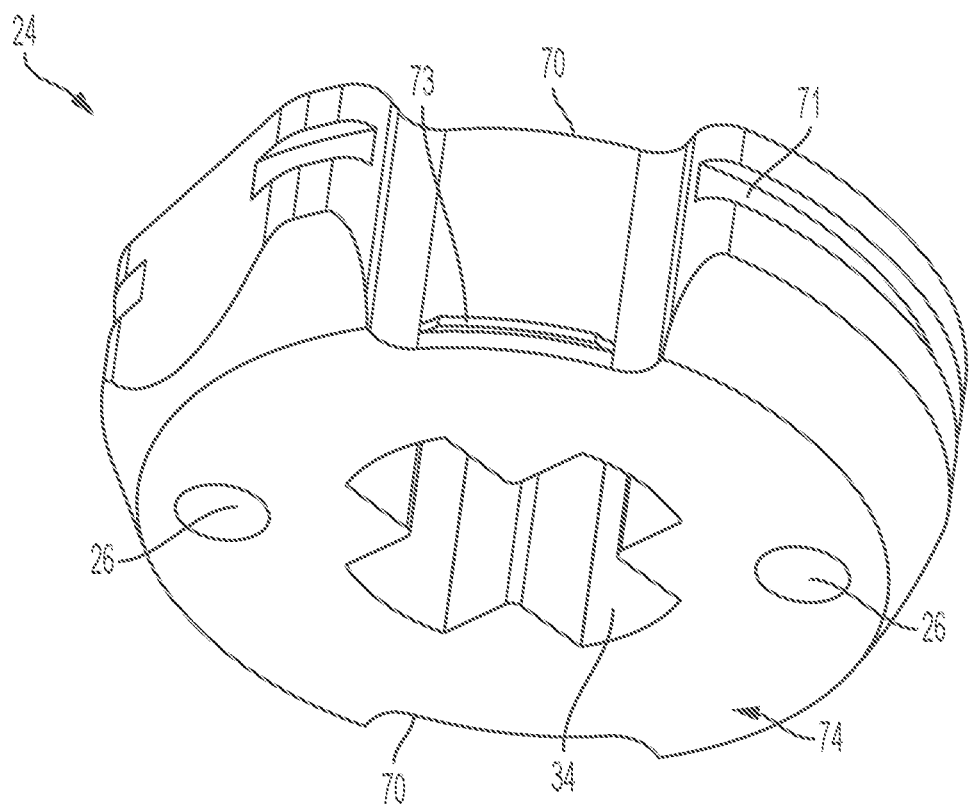

The retaining ring 24 is configured as shown, e.g., in FIGS. 3A, 3B, and 6. The retaining ring has a distal end 68 and a proximal end 74. In accordance with the exemplary embodiment, the proximal end is tapered relative to the distal end. The retaining ring includes a central through hole 34 for receiving the surgical tool. As shown in FIGS. 3A and 3B, the central through hole 34 is illustrated as substantially cross-shaped, although the central through hole 34 may be shaped in any other shape suitable for receiving a surgical tool, such as a triangular, square, pentagonal, hexagonal, heptagonal, or octagonal through hole.

The distal end 68 of the retaining ring 24 is also configured to include a recessed track 35, and preferably two recessed tracks 35, 35'. The number of recessed tracks is chosen to match the number of recessed cams 28 on the locking ring 16. The recessed track is sized and shaped to receive the cam 28 therein such that a bottom-most end of the cam is closely adjacent to or slidingly engages the bottom floor of the recessed track.

Positioned along the recessed track 35 is a through hole 26 for receiving the locking pin 20 into and through the through hole. The through hole 26 has a larger diameter portion toward the distal end of the retaining ring and a smaller diameter portion toward the proximal end, i.e., the through hole can be sloped.

The retaining ring includes at least one indentation 70 configured to receive one or more guide legs 84 of the central ring 44 through the retaining ring, as further discussed below. The indentation includes a flange 73 for mating engagement with the recess 85 of the one or more guide legs 84 of the central ring 44. The retaining ring also includes a retaining track 71. The retaining track 71 defines an annular recess for receiving the retaining band 96.

The retaining ring includes one or more plunger bores 72. The plunger bores 72 are adapted receive the plunger 98 and the biasing member 100, as shown in FIG. 1B.

Figure 4A:
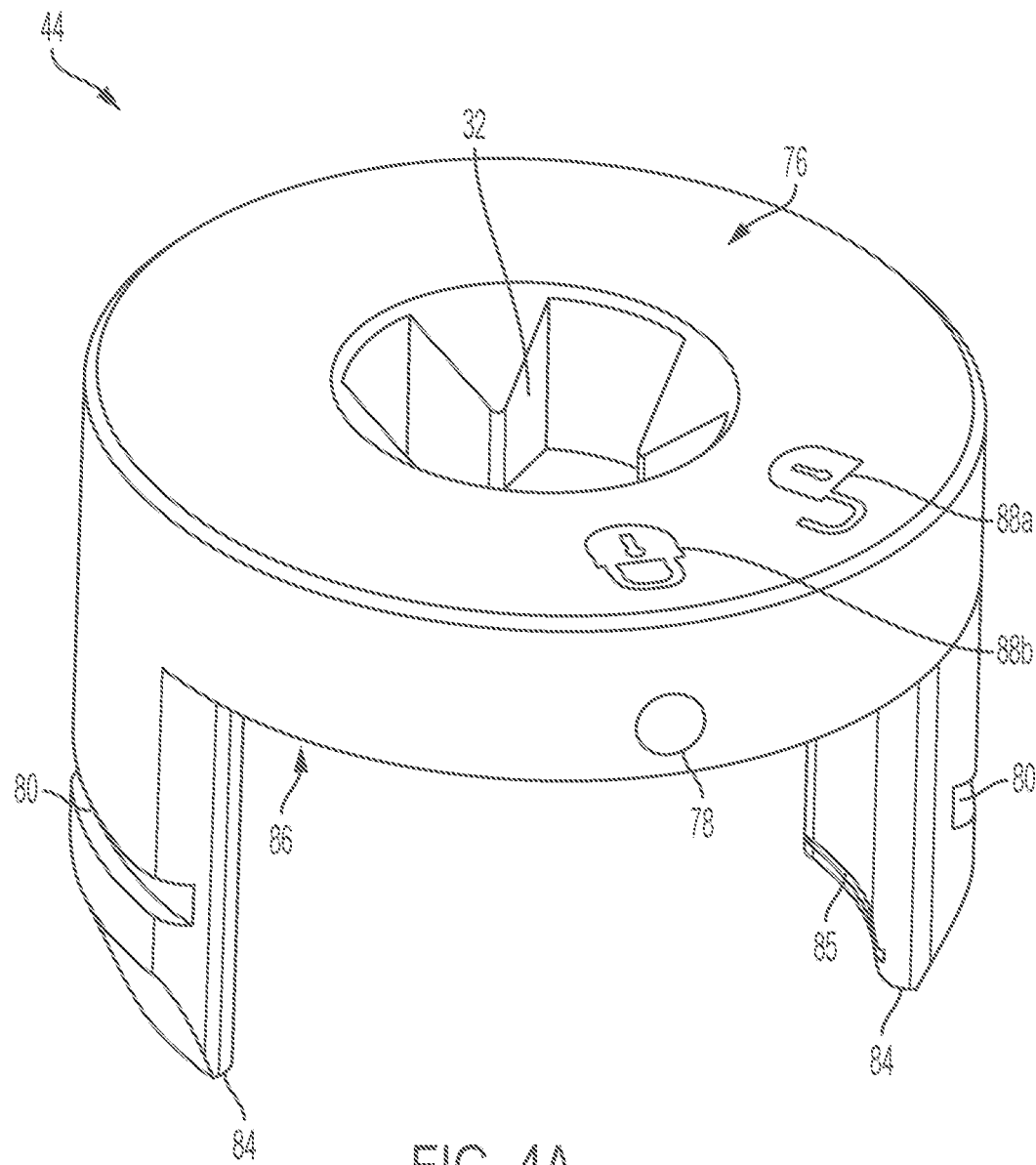
FIGS. 4A-B are various views of a central ring of the handle assembly of FIG. 1A.
Figure 4B:
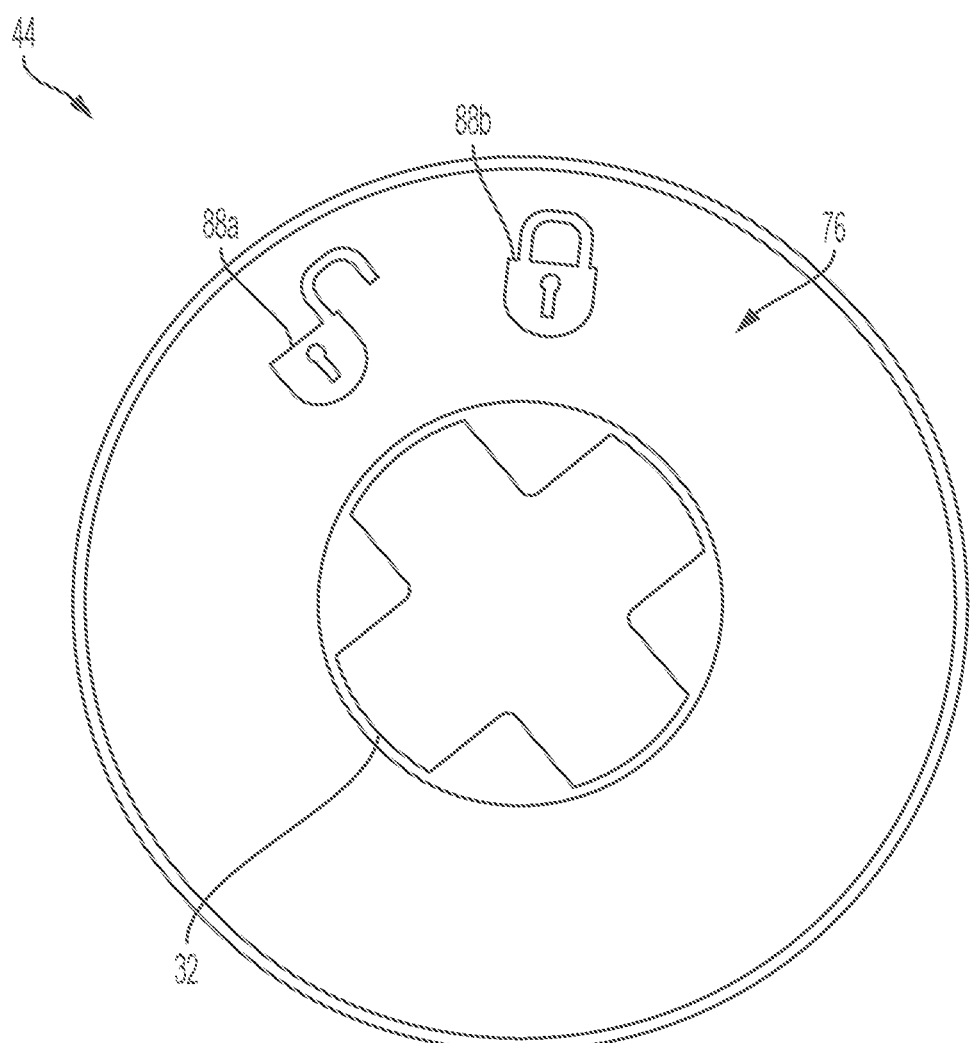

The central ring 44 is configured as shown, e.g., in FIGS. 1A, 1B, 4A, 4B, and 8. The central ring includes a distal end 76 and a proximal end 86. In accordance with the exemplary embodiment, the proximal end includes one or more legs 84. The legs extend proximally from the central ring. The legs are tapered toward the proximal end and disposed opposite each other. The legs include a retaining track 80 and a recess 85. The retaining track 80 is adapted to receive the retaining band 96. The retaining band 96 is adapted to engage the retaining track 71 of the retaining ring 24 and the retaining track 80 of the legs 84, so that the retaining ring 24 and the central ring 44 remain in place relative to each other. The recess 85 is configured for mating engagement with the flange 73 of the retaining ring 24. The central ring includes a central through hole 32 for receiving a surgical tool. As shown in FIGS. 4A and 4B, the central through hole 32 is illustrated as substantially cross-shaped, although the central through hole may be shaped in any other shape suitable for receiving a surgical tool, such as a triangular, square, pentagonal, hexagonal, heptagonal, or octagonal through hole.

The central ring 44 includes one or more status indicators 88a, 88b that operate in concert with the position indicator 60 on the locking ring 16 to indicate whether the locking ring is in the first or second position, as further described below. The central ring also includes a bore or opening 78 that is sized and adapted to receive the pin 46 and the biasing member 48, as shown in FIG. 1B.

Referring to FIGS. 1B and 6, the plate 38 is disposed between the locking ring 16 and the collet 18. The plate is configured as a washer having a central through hole for receiving the surgical tool. The plate is sized to mount within the handle 12.

The biasing member 40 is configured as shown, e.g., in FIGS. 1B and 6. In accordance with the exemplary embodiment, the biasing member 40 may be a compression spring, as shown, or any other suitable biasing member such as an elastomer, leaf spring, plastic, and the like. The biasing member exerts a biasing force distally to bias the collet 18 towards the locking ring 16.

The plunger 98 and the biasing member 100 are configured as shown, e.g., in FIG. 1B. The plunger and biasing member work in concert to exert a biasing force distally against the locking ring 16 and the central ring 44. This biasing force acts to stabilize the handle assembly 10 upon insertion of a tool.

Referring to FIGS. 1B and 6, the retaining ring 24, the plate 38, the collet 18, and the biasing member 40 are all assembled into the tapered receiving cavity 30 of the handle 12. The biasing member 40 is seated with the bottom end of the tapered receiving cavity 30. The collet 18 is disposed distal to or on top of the biasing member and directly engages the biasing member. The plate 38 is disposed distal to the collet 18 and between the collet and the retaining ring 24, and directly engages the collet.

The locking pin 20 is positioned between the locking ring 16 and the plate 38. In accordance with the exemplary embodiment, the locking pin is mounted in the through hole 26 of the retaining ring 24. Due to the overall size of the locking pin, a portion of the top of the locking pin extends proud of the uppermost end of the through hole 26, and a portion of the bottom of the locking pin extends out from the bottom-most end of the through hole and retaining ring.

The plunger 98 and the biasing member 100 are also inserted into the plunger bore 72 of the retaining ring 24. The button 52 is inserted radially inwardly into the bore or opening 50 of the locking ring 16. The locking ring 16 is disposed distal to the retaining ring 24.

Due to the oversizing of the locking pin 20, the locking pin directly engages the cam 28 when the locking ring is moved from its first position to its second position.

The biasing member 48 and the pin 46 are inserted radially inwardly into the bore or opening 78 of the central ring 44. The central ring 44 is seated within the cylindrical indentation 59 of the locking ring 16. Specifically, the legs 84 of the central ring 44 are inserted into and through the guide through holes 62 and into mating engagement with the indentations 70 of the retaining ring 24. Lastly the retaining band 96 is inserted into the retaining track 71 of the retaining ring 24 and the retaining track 80 of the central ring 44. In this regard, the arrangement of the central ring 44, the locking ring 16, the retaining ring 24, and the collet 18 are adapted to bring each central through hole 82, 34, 36, 32 into alignment with each other, thereby allowing the handle assembly 10 to receive a surgical tool smoothly into and through each through hole.

In operation, FIGS. 7A, 7B, and 8 illustrate how the locking ring 16 assumes the first and second positions to receive and then anchor the surgical tool in the locking mechanism 14. When the locking ring is in the first position (e.g., the unlocked position), a user (e.g., a surgeon or other medical provider) may insert a surgical tool into and through the central through holes 32, 34, 36, 82 of the central ring 44, the locking ring 16, the retaining ring 24, and the collet 18, respectively.

Once the surgical tool is properly inserted into the locking ring, retaining ring, and the collet, the user rotates the locking ring 16 to the second position (e.g., the locked position), as shown in FIG. 8. Referring to FIG. 6, when the user rotates the locking ring, the cams 28 cam against the upper surfaces of the locking pins 20, thereby causing the bottom surfaces of the locking pins to press against the plate 38 situated beneath the retaining ring 24. The proximal end of the plate, in turn, presses against the distal end 90 of the collet 18, thereby causing the flexible portion 22 of the collet to be pushed proximally against the tapered wall 42 of the tapered receiving cavity 30. The proximally-directed force on the collet forces the flexible portion of the collet to flex inwardly against the surgical tool, exerting a tight grip on the surgical tool to lock the surgical tool relative to the handle assembly 10. The proximally-directed force on the collet also biases the collet proximally, counter to the biasing force exerted by the biasing member 40, thereby compressing the biasing member.

When the retaining ring 24 is sufficiently turned to the second position such that the lowest portions of the cams 28 are in contact with and camming against the upper surfaces of the locking pins 20, the greatest force is translated from the locking pins 20 to the collet 18 via the plate 38. In the second position, the locking ring 16 locks relative to the center ring 44, thereby locking the surgical tool in position. Referring to FIG. 8, in order to maintain the locking ring 16 locked relative to the center ring 44, when moved to the second position, the pin 46 is biased radially outwardly such that the radially outermost portion of the pin is received in a bore or opening 50 provided on the locking ring 16. When received in the bore 50, the pin 46 is partially within the locking 16 and the center ring 44, thereby preventing rotation of the locking ring 16 relative to the center ring 44. In this position, the surgical tool is both anchored to and locked in the locking mechanism 14.

Referring to FIG. 8, when it is desired to unlock and release the surgical tool from the locking mechanism 14, a user depresses the button lock 52 that is radially disposed on the locking ring 16. Depressing the button lock allows the locking ring to move from the second position (e.g., the locked position) to the first position (e.g., the unlocked position), shown in FIGS. 7A and 7B. As shown in FIG. 8, the radially innermost end 54 of the button lock 52 is contacted by the radially outermost end 56 of the pin 46. Pushing the button lock 52 radially inwardly moves the pin 46 radially inwardly counter to the radially outward biasing force of the biasing member 48. At the point at which the radially outermost end 56 of the pin 46 is pushed out of the bore 50 by the button lock 52, the locking ring 16 is free to rotate relative to the center ring 44. Referring to FIGS. 7A and 7B, the user may then rotate the locking ring 16 to return to the first position (e.g., the unlocked position) relative to the center ring 44. Although shown in accordance with the exemplary embodiment as being turned in a counterclockwise direction to the first position, in accordance with other aspects the locking ring 16 may be turned clockwise to the first position, depending on the direction of slope of the cams 28 on the undersurface of the locking ring 16.

As the locking ring 24 is moved from the second position (e.g., the locked position) shown in FIG. 8 to the first position (e.g., the unlocked position) shown in FIGS. 7A and 7B, the locking pins 20 decompress as they are free from camming engagement with the cams 28. As the locking pins decompress, they exert a reduced force on the plate 38 which, in turn, reduces the force exerted by the flexible portion 22 of the collet 18 against the surgical tool. The reduced force on the plate also reduces the force exerted by the collet against the biasing member 40, thereby allowing the biasing member to bias the collet distally toward the locking ring 16. When the locking ring reaches the first position, the force exerted by the locking pins on the plate 38 is essentially minimal. In such a state, the flexible portion 22 of the collet 18 relaxes from clamping engagement with the surgical tool, whereby the surgical tool may be readily extracted from the locking mechanism 14.

The exemplary embodiments of the handle assembly discussed herein provide numerous advantages over conventional surgical tool handles. For example, the handle assembly 10 eliminates play of the surgical tool within the handle. The handle assembly thus greatly enhances user control of the knee osteotome or other surgical tool during a surgical procedure. Further, it is to be understood that while the present disclosure is useful for firmly holding a knee osteotome, the handle assembly disclosed herein is equally suitable to firmly holding different types of surgical tools or other tools.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

I claim:

1. A handle assembly for receiving a tool comprising:
   a primary handle; and
   an attachment mechanism attached to the primary handle, the attachment mechanism including:
   a locking handle rotatable relative to the primary handle, and a fastener operatively engaged with the locking handle for moving between a locking position and an unlocking position;
   wherein the attachment mechanism further comprises a retaining ring having a through hole for receiving the fastener;
   wherein the locking handle includes a cam for camming against the fastener.

2. The handle assembly of claim 1, wherein the attachment mechanism further comprises a collet mounted to the primary handle.

3. The handle assembly of claim 2, wherein the collet includes a flexible portion movable between a first position and a second position.

4. The handle assembly of claim 1, wherein the primary handle includes a cavity, and the collet is mounted within the cavity.

5. The handle assembly of claim 4, wherein the cavity is a tapered cavity.

6. The handle assembly of claim 3, wherein when the locking handle rotates, it moves the flexible portion of the collet from the first position to the second position.

7. The handle assembly of claim 2, wherein the fastener is between the locking handle and the collet.

8. The handle assembly of claim 1, wherein the fastener comprises at least one of nylon, polytetrafluoroethylene, ultra-high molecular weight polyethylene, polyetherimide, and glass.

9. The handle assembly of claim 1, wherein the fastener is mounted in the through hole and oversized relative to a size of the through hole.

10. The handle assembly of claim 1, wherein the fastener is mounted in the through hole and has an overall height greater than an overall height of the retaining ring.

\* \* \* \* \*